United States Patent [19] [11] 3,974,276
Barlow et al. [45] Aug. 10, 1976

[54] CERTAIN DIAZINES AS PLANT PESTICIDES

[75] Inventors: Charles Brian Barlow, Camberley; Brian Graham White, Crowthorne; Clive Dudley Spencer Tomlin, Maidenhead, all of England

[73] Assignee: Imperial Chemical Industries Limited, London, England

[22] Filed: Apr. 28, 1975

[21] Appl. No.: 572,830

Related U.S. Application Data

[62] Division of Ser. No. 230,513, Feb. 29, 1972, Pat. No. 3,906,098.

[30] Foreign Application Priority Data

Mar. 19, 1971 United Kingdom............ 7289/71
Mar. 19, 1971 United Kingdom............ 7290/71
Mar. 19, 1971 United Kingdom............ 7293/71

[52] U.S. Cl. ........................ 424/250; 424/251; 71/67; 71/92; 260/250 R
[51] Int. Cl.² ........................ A01N 9/22
[58] Field of Search ............ 424/250, 251

[56] References Cited
UNITED STATES PATENTS 3,499,898   3/1970   von Bebenbutg et al. ........... 424/251

Primary Examiner—V. D. Turner
Attorney, Agent, or Firm—Cushman, Darby & Cushman

[57] ABSTRACT

Compositions and methods for combatting insects, fungal and bacterial plant pests are disclosed wherein the active ingredient is a compound of the formula Z—NH—Y wherein X is selected from the group consisting of a pyrazinyl radical bearing one to three substitutents, and pyrimidinyl and pyridazinyl radicals bearing two to three substituents; and Y represents phenyl, naphthyl, pyridyl or diazinyl bearing at least one substituent; the substituents in each case selected from the group consisting of halogen, cyano, nitro, trifluoromethyl, lower alkoxy, lower alkylthio, benzylthio, lower alkyl and amino, provided that (a) the compound bears at least four substituents of which at least two are halogen atoms, and (b) where X represents a pyrimidinyl radical and Y represents a pyridyl radical there is at least one substituent other than halogen present.

4 Claims, No Drawings

CERTAIN DIAZINES AS PLANT PESTICIDES

This is a division of application Ser. No. 230,513, filed Feb. 29, 1972, now U.S. Pat. No. 3,906,098.

This invention relates to novel heterocyclic derivatives and to processes for preparing them. In a further aspect this invention relates to compositions comprising the novel compounds and to methods of combatting pests, especially pests of plants. More particularly the invention relates to diazine derivatives, processes for preparing them, compositions comprising them and methods of combatting pests using them.

The term "diazine derivative" is used herein to signify a compound which incorporates within its structure a six-membered aromatic heterocycle containing two nitrogen atoms and four carbon atoms. Three such heterocycles are possible, namely a 1,2-diazine hereinafter referred to as pyridazine, a 1,3-diazine hereinafter referred to as pyrimidine, and a 1,4-diazine hereinafter referred to as pyrazine.

Accordingly the present invention provides a compound of formula:

X—NH—Y wherein X represents a pyrazinyl radical bearing at least one substituent, or a pyrimidinyl or pyridazinyl radical bearing at least two substituents; and Y represents an aryl, pyridyl or diazinyl radical, bearing at least one substituent; the substituents in each case being selected from halogen atoms, and cyano, nitro, perhaloalkyl, alkoxy, alkylthio, aralkylthio and amino groups; provided that (a) there are at least four substituents present of which at least two are halogen atoms and (b) where X represents a pyrimidinyl radical and Y represents a pyridyl radical there is at least one substituent other than halogen present.

In a preferred aspect the invention provides compounds of formula:

X—NH—Y wherein X represents a diazinyl radical bearing at least two substituents selected from halogen atoms, and cyano, perhaloalkyl, alkyl and aralkylthio groups; and Y represents an aryl, pyridyl or diazinyl radical, bearing at least one substituent selected from halogen atoms, and cyano, nitro, perhaloalkyl, alkyl, alkoxy, alkylthio, aralkylthio and amino groups; provided that (a) there are at least four substituents present of which at least two are halogen atoms, and (b) where X represents a pyrimidinyl radical and Y represents a pyridyl radical there is at least one substituent other than halogen present.

In a more preferred aspect the invention provides compounds of formula:

X—NH—Y wherein X represents a diazinyl radical bearing at least two substituents selected from fluorine and chlorine atoms, and cyano, trifluoromethyl, methyl and benzylthio groups; and Y represents an aryl, pyridyl or diazinyl radical bearing at least one substituent selected from fluorine, chlorine and bromine atoms, and cyano, nitro, trifluoromethyl, methyl, methoxy, methylthio, benzylthio and amino groups; provided that (a) at least four substituents are present of which at least two are fluorine or chlorine, and (b) where X represents a pyrimidinyl radical and Y represents a pyridyl radical there is at least one substituent other than chlorine, fluorine or bromine present.

In a first even more preferred aspect the invention provides compounds of formula:

X—NH—Y wherein X represents a diazinyl radical, which is substituted with halogen atoms or cyano or perhaloalkyl groups; and Y represents an aryl radical which is substituted with halogen atoms, or nitro, cyano, or perhaloalkyl groups; provided that at least four substituents are present of which at least two are halogen atoms.

In a second even more preferred aspect the invention provides compounds of formula:

X—NH—Y wherein X represents a diazinyl radical; and Y represents a pyridyl radical; and wherein the diazinyl and pyridyl radicals are substituted by halogen atoms, or cyano, nitro, perhaloalkyl, alkyl alkoxy, alkylthio, aralkylthio or amino groups; provided that (a) at least four substituents are present of which at least two are halogen atoms, and (b) where X represents a pyrimidinyl radical there is at least one substituent other than halogen present.

In a third even more preferred aspect the invention provides compounds of formula:

X—NH—Y wherein X and Y, which may be the same or different, represent diazinyl radicals, substituted with halogen atoms, or cyano, perhaloalkyl or alkyl groups; provided that at least four substituents are present of which at least two are halogen atoms.

In a first even yet more preferred aspect the invention provides compounds of formula:

X—NH—Y wherein X represents a pyrimidinyl radical bearing at least two substituents selected from halogen atoms, and cyano, perhaloalkyl and aralkylthio groups; and Y represents a naphthyl radical, or a phenyl radical bearing at least two substituents selected from halogen atoms and cyano, nitro, and trifluoromethyl groups.

In a second even yet more preferred aspect the invention provides compounds of formula:

X—NH—Y wherein X represents a pyrimidinyl radical bearing at least two substituents selected from halogen atoms, and cyano, perhaloalkyl, alkyl and aralkylthio groups; and Y represents a pyridyl radical bearing four substituents selected from halogen atoms, and alkoxy, alkylthio, and amino groups; provided that there is present at least one substituent other than halogen.

In a third even yet more preferred aspect the invention provides compounds of formula:

X—NH—Y wherein X represents a pyrimidinyl radical, bearing at least two halogen substituents; and Y represent a pyrimidine radical bearing at least two substituents selected from halogen atoms, and cyano and alkyl groups.

In a fourth even yet more preferred aspect the invention provides compounds of formula:

X—NH—Y wherein X represents a pyridazinyl radical bearing at least two halogen substituents; and Y represents a phenyl radical bearing at least two substituents selected from halogen atoms, and cyano, nitro and perfluoroalkyl groups.

In a fifth even yet more preferred aspect the invention provides compounds of formula:

X—NH—Y wherein X represents a pyridazinyl radical bearing three halogen substituents; and Y represents a pyridyl radical bearing four substituents selected from halogen atoms and alkoxy groups.

In a sixth even yet more preferred aspect the invention provides compounds of formula:

X—NH—Y wherein X represents a pyrazinyl radical bearing three halogen atoms; and Y represents a phenyl radical bearing at least two substituents selected from halogen atoms, cyano, nitro and perhaloalkyl groups.

In a seventh even yet more preferred aspect the invention provides compounds of formula:

X—NH—Y wherein X represents a pyrazinyl radical bearing at least one halogen atom; and Y represents a pyridyl radical bearing four substituents selected from halogen atoms and alkoxy groups.

In an eighth even yet more preferred aspect the invention provides compounds of formula:

X—NH—Y wherein X represents a pyrazinyl radical bearing at least one halogen atom and Y represents a pyrazinyl radical bearing three halogen atoms.

Preferred halogen atom substituents for any of the above compounds are chlorine and fluorine. Fluorine is an especially preferred substituent for aryl and pyridyl radicals and chlorine an especially preferred substituent for pyrimidinyl radicals.

The structural formulae of compounds illustrative of the present invention are set out in Table I below, together with a melting point for each compound.

TABLE I

| Compound No: | Structural Formula | Melting Point °C |
|---|---|---|
| 1 | 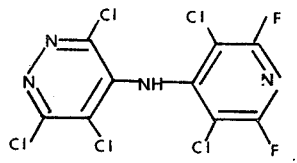 | 139 |
| 2 | 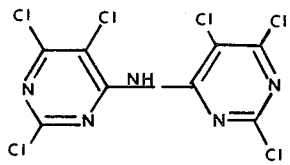 | >300 |
| 3 | 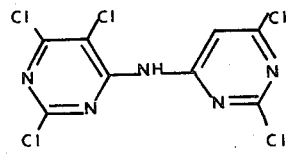 | 175–177 |
| 4 | 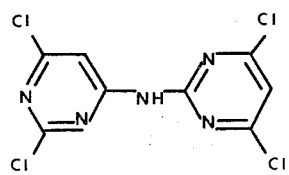 | 166.8–168.3 |

TABLE I-continued

| Compound No: | Structural Formula | Melting Point °C |
|---|---|---|
| 5 | 2,5,6-trichloropyrimidin-4-yl-NH-4,6-dichloropyrimidin-2-yl | 179.8–181.6 |
| 6 | 2,5,6-trichloropyrimidin-4-yl-NH-(2,3,5,6-tetrafluoro-4-trifluoromethylphenyl) | 151.4–153.0 |
| 7 | 2,5,6-trichloropyrimidin-4-yl-NH-(2,3,5,6-tetrafluoro-4-cyanophenyl) | 133–135 |
| 8 | trifluoropyrazinyl-NH-(2,3,5,6-tetrafluoro-4-cyanophenyl) | 136.5–157.8 |
| 9 | 2,5,6-trichloropyrimidin-4-yl-NH-pentafluorophenyl | 136.0–136.4 |
| 10 | 2,5,6-trichloropyrimidin-4-yl-NH-4,6-dichloropyrimidin-5-yl | 189.5–192.2 |
| 11 | 2,6-dichloropyrimidin-4-yl-NH-pentafluorophenyl | 156.7–157.7 |

TABLE I-continued

| Compound No: | Structural Formula | Melting Point °C |
|---|---|---|
| 12 | (2,6-dichloro-5-chloropyrimidin-4-yl)-NH-(2,3,5,6-tetrafluoro-4-nitrophenyl) | 157.6–161.1 |
| 13 | (2,6-dichloro-5-chloropyrimidin-4-yl)-NH-(2-trifluoromethyl-4-nitrophenyl) | 159.0–162.5 |
| 14 | (4,6-dichloropyrimidin-5-yl)-NH-(2,3,5,6-tetrafluoro-4-cyanophenyl) | 132.8–134.6 |
| 15 | (2,6-dichloro-5-chloropyrimidin-4-yl)-NH-(heptafluoronaphth-2-yl) or α-naphthyl isomer | 152.2–154.7 |
| 16 | (3,6-dichloro-5-chloropyridazin-4-yl)-NH-(2,3,5,6-tetrafluoro-4-cyanophenyl) or 3-pyridazinyl isomer | 198.7–200.1 |

TABLE I-continued

| Compound No: | Structural Formula | Melting Point °C |
|---|---|---|
| 17 | (3,6-dichloropyridazin-4-yl)-NH-(2,3,5,6-tetrafluoro-4-cyanophenyl); or 3- or 4-pyridazinyl isomer | 210 |
| 18 | (3,6-difluoro-5-fluoropyrazin-2-yl)-NH-(3,5-dichloro-2,6-difluoropyridin-4-yl) | 116 |
| 19 | (4,6-dichloropyrimidin-5-yl)-NH-(2-trifluoromethyl-4-nitrophenyl) | 147.0–147.6 |
| 20 | (4,6-dichloropyrimidin-5-yl)-NH-(2,3,5,6-tetrafluoro-4-nitrophenyl) | 112.2–114.2 |
| 21 | (2,5,6-trichloropyrimidin-4-yl)-NH-(5-cyano-2-methylpyrimidin-4-yl) | 162.1–163.0 |
| 22 | (5-chloropyrazin-2-yl)-NH-(3,5-dichloro-2,6-difluoropyridin-4-yl) | 174.9–176.3 |

TABLE I-continued

| Compound No: | Structural Formula | Melting Point °C |
|---|---|---|
| 23 | 4-[(3,5-dichloro-2,6-difluoropyridin-4-yl)amino]-2-methylpyrimidine-5-carbonitrile | 177.3–178.4 |
| 24 | 2,6-dichloro-N-(2,3,5,6-tetrafluoro-4-(trifluoromethyl)phenyl)pyrimidin-4-amine | 187.0–187.5 |
| 25 | 4-((2,6-dichloropyrimidin-4-yl)amino)-2,3,5,6-tetrafluorobenzonitrile | 162.6–165.6 |
| 26 | 2,5,6-trichloro-N-(3,5-dichloro-2-fluoro-6-(methylthio)pyridin-4-yl)pyrimidin-4-amine | 166.0–167.0 |
| 27 | 2-(benzylthio)-4-((3,5-dichloro-2,6-difluoropyridin-4-yl)amino)pyrimidine-5-carbonitrile | 226.4–230.4 |
| 28 | 2,5,6-trichloro-N-(3,5-dichloro-2-fluoro-6-methoxypyridin-4-yl)pyrimidin-4-amine | 172.3–174.2 |

TABLE I-continued

| Compound No: | Structural Formula | Melting Point °C |
|---|---|---|
| 29 | (4,5,6-trichloropyrimidin-4-yl)-NH-(2-bromo-4-nitrophenyl) | 146.0–148.0 |
| 30 | (3,5,6-trifluoropyrazin-2-yl)-NH-(2-trifluoromethyl-4-nitrophenyl) | 126.7–128.3 |
| 31 | (3,5,6-trifluoropyridazin-4-yl)-NH-(3,5-dichloro-2,6-difluoropyridin-4-yl) | 122.3–122.7 |
| 32 | (3,5,6-trifluoropyridazin-4-yl)-NH-(2-trifluoromethyl-4-nitrophenyl) | 123.6–124.4 |
| 33 | (6-chloropyrazin-2-yl)-NH-(3,5,6-trifluoropyrazin-2-yl) | 189.0–190.0 |
| 34 | (2,5,6-trichloropyrimidin-4-yl)-NH-(3,5-dichloro-6-fluoro-2-aminopyridin-4-yl) (Mixture with 2-pyridyl isomer) | 123–133 |
| 35 | (5-cyano-2-trifluoromethylpyrimidin-4-yl)-NH-(2,3,5,6-tetrafluoro-4-cyanophenyl) | 170–171 |

TABLE I-continued

| Compound No: | Structural Formula | Melting Point °C |
|---|---|---|
| 36 | (pyrimidine with CN, CF₃)–NH–(pyridine with Cl, Cl, F, F) | 185–186 |
| 37 | (pyrimidine with CN, C₆H₅CH₂S)–NH–(benzene with F, F, F, F, CN) | 191–192 |
| 38 | (pyrimidine with Cl, CF₃)–NH–(pyridine with Cl, Cl, F, F) | 151.1–154.6 |
| 39 | (pyrimidine with F, F, F)–NH–(pyridine with Cl, Cl, F, OCH₃) | 111.7–113.2 |
| 40 | (pyridazine with F, F, F)–NH–(pyridine with Cl, Cl, F, OCH₃) | 173.2–174.0 |

The compounds of the present invention are conveniently prepared by treating a compound of the formula:

$$X-NH_2$$

with a base, and subsequently reacting the treated compound thus produced with a compound of the formula:

$$Y-Hal$$

wherein X and Y have any of the meanings hereinbefore defined and Hal represents an atom of halogen.

In an alternative procedure the compounds of the present invention may be prepared by treating a compound of the formula:

Y—NH₂ with a base, and subsequently reacting the treated compound thus produced with a compound of the formula:

X—Hal wherein X, Y and Hal have any of the meanings hereinbefore defined.

A suitable base for use in the above reactions is sodium hydride, and the process may be carried out in a diluent or solvent, for example, dimethylformamide.

The compounds of the invention may be used as pesticides either on their own or, preferably, incorporated in a composition comprising a diluent in addition to the invention compound.

Accordingly the present invention further provides a pesticidal composition comprising a compound of formula:

X—NH—Y wherein X represents a pyrazinyl radical bearing at least one substituent or a pyrimidinyl or pyridazinyl radical bearing at least two substituents; and Y represents an aryl, pyridyl or diazinyl radical, bearing at least one substituent; the substituents in each case being selected from halogen atoms, and cyano, nitro, perhaloalkyl, alkoxy, alkylthio, aralkylthio and amino groups; provided that (a) there are at least four substituents present of which at least two are halogen atoms, and (b) where X represents a pyrimidinyl radical and Y represents a pyridyl radical there is at least one substituent other than halogen present.

In a preferred aspect the invention provides pesticidal compositions comprising a compound of formula:

X—NH—Y wherein X represents a diazinyl radical bearing at least two substituents selected from halogen atoms, and cyano, perhaloalkyl, alkyl and aralkylthio groups; and Y represents an aryl, pyridyl or diazinyl radical, bearing at least one substituent selected from halogen atoms, and cyano, nitro, perhaloalkyl, alkyl, alkoxy, alkylthio, aralkylthio and amino groups; provided that (a) there are at least four substituents present of which at least two are halogen atoms, and (b) where X represents a pyrimidinyl radical and Y represents a pyridyl radical there is at least one substituent other than halogen present.

In a more preferred aspect the invention provides pesticidal compositions comprising a compound of formula:

X—NH—Y wherein X represents a diazinyl radical bearing at least two substituents selected from fluorine and chlorine atoms, and cyano, trifluoromethyl, methyl and benzylthio groups; and Y represents an aryl, pyridyl or diazinyl radical bearing at least one substituent selected from fluorine, chlorine and bromine atoms, and cyano, nitro, trifluoromethyl, methyl, methoxy, methylthio, benzylthio and amino groups; provided that (a) at least four substituents are present of which at least two are fluorine or chlorine, and (b) where X represents a pyrimidinyl radical and Y represents a pyridyl radical there is at least one substituent other than chlorine, fluorine or bromine present.

In a first even more preferred aspect the invention provides pesticidal compositions comprising a compound of formula:

X—NH—Y wherein X represents a diazinyl radical, which is substituted with halogen atoms or cyano or perhaloalkyl groups; and Y represents an aryl radical which substituted with halogen atoms, or nitro, cyano, or perhaloalkyl groups; provided that at least four substituents are present of which at least two are halogen atoms.

In a second even more preferred aspect the invention provides pesticidal compositions comprising a compound of formula:

X—NH—Y wherein X represents a diazinyl radical; and Y represents a pyridyl radical; and wherein the diazinyl and pyridyl radicals are substituted by halogen atoms, or cyano, nitro, perhaloalkyi, alkyl alkoxy, alkylthio, aralkylthio or amino groups; provided that (a) at least four substituents are present of which at least two are halogen atoms, and (b) where X represents a pyrimidinyl radical there is at least one substituent other than halogen present.

In a third even more preferred aspect the invention provides pesticidal compositions comprising a compound of formula:

X—NH—Y wherein X and Y, which may be the same or different, represent diazinyl radicals, substituted with halogen atoms, or cyano, perhaloalkyl or alkyl groups; provided that at least four substituents are present of which at least two are halogen atoms.

In a first even yet more preferred aspect the invention provides pesticidal compositions comprising a compound of formula:

X—NH—Y wherein X represents a pyrimidinyl radical bearing at least two substituents selected from halogen atoms, and cyano, perhaloalkyl and aralkylthio groups; and Y represents a naphthyl radical, or a phenyl radical, bearing at least two substituents selected from halogen atoms and cyano, nitro, and perfluoroalkyl groups.

In a second even yet more preferred aspect the invention provides pesticidal compositions comprising a compound of formula:

X—NH—Y wherein X represents a pyrimidinyl radical bearing at least two substituents selected from halogen atoms, and cyano, perhaloalkyl, alkyl and aralkylthio groups; and Y represents a pyridyl radical bearing four substituents selected from halogen atoms, and alkoxy, alkylthio, and amino groups; provided that there is present at least one substituent other than halogen.

In a third even yet more preferred aspect the invention provides pesticidal compositions comprising a compound of formula:

X—NH—Y wherein X represents a pyrimidinyl radical, bearing at least two halogen substituents; and Y represent a pyrimidine radical bearing at least two substituents selected from halogen atoms, and cyano and alkyl groups.

In a fourth even yet more preferred aspect the invention provides pesticidal compositions comprising a compound of formula:

X—NH—Y wherein X represents a pyridazinyl radical bearing at least two halogen substituents; and Y represents a phenyl radical bearing at least two substituents selected from halogen atoms, and cyano, nitro and perfluoroalkyl groups. In a fifth even yet more preferred aspect the invention provides pesticidal compositions comprising a compound of formula:

X—NH—Y wherein X represents a pyridazinyl radical bearing three halogen substituents; and Y represents a pyridyl radical bearing four substituents selected from halogen atoms and alkoxy groups.

In a sixth even yet more preferred aspect the invention provides pesticidal compositions comprising a compound of formula:

X—NH—Y wherein X represents a pyrazinyl radical bearing three halogen atoms; and Y represents a phenyl radical bearing at least two substituents selected from halogen atoms, cyano, nitro and perhaloalkyl groups.

In a seventh even yet more preferred aspect the invention provides pesticidal compositions comprising a compound of formula:

X—NH—Y wherein X represents a pyrazinyl radical bearing at least one halogen atom; and Y represents a pyridyl radical bearing four substituents selected from halogen atoms and alkoxy groups.

In an eighth even yet more preferred aspect the invention provides pesticidal compositions comprising a compound of formula:

X—NH—Y wherein X represents a pyrazinyl radical bearing at least one halogen atom and Y represents a pyrazinyl radical bearing three halogen atoms.

Compounds of the invention and compositions comprising them are toxic towards insect and other invertebrate pests, including for example the following:

| | |
|---|---|
| *Tetranychus telarius* | (red spider mites) |
| *Plutella maculipennis* | (diamond back moth) |
| *Aphis fabae* | (black aphids) |
| *Pieris brassicae* | (cabbage white caterpiller) |
| *Blattella germanica* (cockroaches) | |
| *Megoura viciae* | (green aphids) |
| *Phaedon cochleariae* | (mustard beetles) |
| *Musca domestica* | (houseflies) |
| *Aedes aegypti* | (mosquitos) |
| *Agriolimax reticulatus* | (greyfield slug) |
| *Meloidogyne incognita* | (nematodes) |
| *Calandra granaria* | (grain weevils) |

The compounds of the invention, and compositions comprising them, possess activity against a wide variety of plant foliar and post-harvest fungal and bacterial diseases including, for example the following specific diseases:

| | | |
|---|---|---|
| *Sphaerotheoa fuliginea* | (powdery mildew) | on cucumber |
| *Puccinia recondita* | (rust) | on tomatoes |
| *Botrytis cinerea* | (chocolate spot) | on broad beans |
| *Phytophthora infestans* | (late blight) | on broad beans |
| *Podosphaera leucotricha* | (powdery mildew) | on apple |
| *Uncinula necator* | (powdery mildew) | on vine |
| *Piricularia oryzae* | (blast) | on rice |
| *Plasmopara viticola* | (downy mildew) | on vine |
| *Venturia inaequalis* | (scab) | on apple |
| *Botrytis tulipae* | (fire) | on bulbs |
| *Nigrospora sphaerica* | (squirter) | on bananas |
| *Phomopsis citri* | (scab) | on citrus |
| *Alternaria citri* | (end rot) | on citrus |
| *Phytophthora citrophthora* | (brown rot) | on citrus |
| *Penicillium digitatum* | (green mould) | on citrus |
| *Gloeosporium musarum* | (black end) | on bananas |
| *Fusarium caeruleum* | (dry rot) | on potatoes |
| *Botrodiplodia theobromae* | (stalk rot) | on bananas |
| *Ceratocystis paradoxa* | (gangrene) | on potatoes |
| *Phoma exigua* | (rot) | on pineapple |
| *Phytophthora parasitica* | (grey mould) | on citrus |
| *Xanthomonas oryzae* | (bacterial leaf blight) | on rice |
| *Xanthomonas malvacearum* | (blackarm) | on cotton |
| *Erwinia amylovora* | (fire blight) | on pears and apples |
| *Erwinia carotovora* | (bacterial soft rot) | of vegetables |
| *Pseudomonas phaseolicola* | (hale blight) | on beans |
| *Pseudomonas syringae* | (dieback) | of stone fruit |
| *Pseudomonas mors-prunorum* | (bacterial canker) | of stone fruit |
| *Corynebacterium michinganense* | (bacterial canker) | |
| *Streptomyces scabies* | (scab) | on potatoes |
| *Agrobacterium tumefaciens* | (crown gall) | |

The invention compounds also display herbicidal activity and are preferably used at higher rates of application for this purpose. The compounds are also algicidal.

In use, the invention compounds, or compositions containing them may be used to combat pests in a variety of ways. Thus the pests themselves, or the locus of the pests, or the pest habitat may be treated to control the pests.

In a further feature therefore the invention provides a method of combating pests wherein the pests, the locus of the pests, or the habitat of the pests is treated with a compound or a composition according to the invention.

The invention also provides a method of treating plants with a compound or composition according to the invention to render them less susceptible to damage by pests, which may already be occurring (i.e. treatment to eradicate an infestation or infection) or which are expected to occur (i.e. treatment to protect the plant from an infestation or infection).

In a yet further feature, therefore, the invention provides a method of treating plants to render them less susceptible to damage by pests, which comprises treating the plants, or the seeds, corms, bulbs, tubers, rhizomes or other propagative parts of the plants with a compound or composition according to the invention.

If desired the medium in which the plants are growing may be similarly treated with a compound or composition according to the invention.

In another feature, therefore the invention provides a method of treating a medium in which plants are growing or to be grown which comprises applying to the medium a compound or composition according to the invention.

The compounds and compositions of the invention may be used for agricultural or horticultural purposes and the compound or type of composition used in any instance will depend upon the particular purpose for which it is to be used.

Compositions comprising the invention compounds may be in the form of dusting powders or granules wherein the active ingredient is mixed with a solid diluent or carrier. Suitable solid diluents or carriers may be, for example kaolinite (china clay), montmorillonite, attapulgite, talc, pumice, silica, calcium carbonate, gypsum, powdered magnesia, Fuller's earth, Hewitt's earth and diatomaceous earth. Compositions for dressing seed, for example, may comprise an agent assisting the adhesion of the composition to the seed, for example, a mineral oil.

The composition may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic, or non-ionic type. Suitable agents of the cationic type include, for example, quaternary ammonium compounds, for example cetyltrimethylammonium bromide. Suitable agents of the anionio type include, for example, soaps, salts of aliphatic monoesters of sulphuric acid, for example sodium lauryl sulphate, salts of sulphonated aromatic compounds, for example sodium dodecylbenzenesulphonate, sodium calcium, or ammonium lignosulphonate, butylnaphthalene sulphonate, and a mixture of the sodium salts of diisopropyl- and triisopropylnaphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides. The condensation products of the said partial esters with ethylene oxide, the lecithins, and block copolymers of ethylene oxide and propylene oxide.

Suitable suspending agents are, for example, bentonite, pyrogenic silica, and hydrophilic colloids, for example polyvinylpyrrolidone and sodium carboxymethylcellulose, and the vegetable gums, for example gum acacia and gum tragacanth.

The aqueous solutions dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compounds of the invention may also be formulated into compositions comprising capsules or microcapsules containing either the active ingredient itself, or a composition containing the active ingredient, and prepared by any of the known encapsulation or microencapsulation techniques.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example, for improving the distribution, adhesive power and resistance to rain on treated surfaces, the different compositions can be better adapted for the various uses for which they are intended.

The compounds of this invention may also be conveniently formulated by admixing them with fertilizer material incorporating, for example coated with, a compound of the invention. The fertilizer material may, for example, comprise nitrogen or phosphate-containing substances.

In yet a further aspect of the invention, therefore, we provide a pesticidal composition comprising as an active ingredient a compound of the invention in admixture with a fertilizer material.

The compositions which are to be used in the form of aqueous dispersions or emulsions are generally supplied in the form of a concentrate containing a high proportion of the active ingredient or ingredients, the said concentrate to be diluted with water before use.

These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 10–85% by weight of the active ingredient or ingredients and generally from 25–60% by weight of the active ingredient or ingredients. When diluted to form aqueous preparations, such preparations may contain varying amounts of the active ingredient or ingredients depending upon the purpose for which they are to be used, but an aqueous preparation containing between 0.001% and 1.0% by weight of the active ingredient or ingredients may be used.

It is to be understood that the pesticidal compositions of this invention may comprise, in addition to a compound of the invention, one or more other compounds having biological activity.

The invention is illustrated, but not limited, by the following examples.

EXAMPLE 1

This example illustrates the preparation of 4(2,3,5,6-tetrafluoro-4-trifluoromethylanilino)2,5,6-trichloropyrimidine (Comound No. 6 of Table I) having the formula:

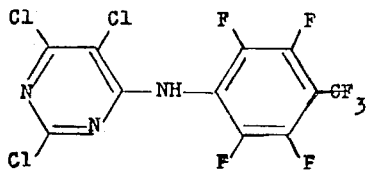

4-Amino-2,5,6-trichloropyrimidine (1.98 g) was dissolved in dry dimethylformamide (25 cc) and the solution added dropwise to a stirred suspension of sodium hydride (0.5 g) in dry dimethylformamide (25 cc) under a nitrogen atmosphere at 0°C. When the addition was complete and evolution of hydrogen had ceased a solution of octafluorotoluene (2.4 g) in dry dimethylformamide (15 cc) was added dropwise to the mixture at 0°C. When this addition was complete the mixture was stirred for 30 minutes, and the temperature allowed to rise to 21°C. The mixture was then poured into a mixture of iced water and salt (400 cc) and acidified with dilute hydrochloric acid.

The gummy precipitate which was formed slowly hardened on standing (18 hours) and was twice recrystallised from a mixture of methylene chloride and petroleum ether (boiling range 40°–60°C) to yield 4(2,3,5,6-tetrafluoro-4-trifluoromethylanilino)-2,5,6-trichloropyrimidine, having a melting point of 152.4° to 153°C.

EXAMPLE 2

This Example illustrates the preparation of 2,2',5-,5',6,6'-hexachloro-4,4'-dipyrimidinylamine (Compound No. 2 of Table I) having the structure:

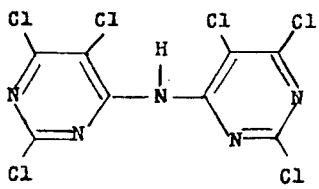

4-Amino-2,5,6-trichloropyrimidine (0.9 gm.) was dissolved in dry dimethylformamide (10 ml.) and the solution added to a stirred suspension of sodium hydride (0.58 gm.) in dry dimethylformamide (15 ml.), under a nitrogen atmosphere at a temperature between 0° and 5°C. The mixture became pale green and a slight temperature rise and effervescence was observed. When the addition was complete and evolution of hydrogen had ceased, a solution of 2,4,5,6-tetrachloropyrimidine (1.1 gm.) in dry dimethylformamide (15 ml.) was added dropwise to the mixture. Some effervescence was observed during the addition, and when the addition was complete the mixture was stirred for a further hour, the temperature of the mixture being allowed to rise during this period to 18°C. The excess sodium hydride was then decomposed with a little water before the mixture was poured onto ice with stirring. Acidification of the aqueous mixture produced a white precipitate which was filtered off and recrystalised from petroleum ether (boiling range 100° to 120°C) to yield 2,2',5,5',6,6'-hexachloro-4,4'-dipyrimidinylamine, having a melting point greater than 300°C.

EXAMPLE 3

The procedures illustrated in Examples 1 and 2 were used to prepare other compounds of the invention from the appropriate reactants as set out below:

4(3,5 Dichloro-2,6-difluoropyrid-4-ylamino)-3,5,6-trichloropyridazine (Compound No. 1, Table I) from 4-amino-3,5-dichloro-2,6-difluoropyridine, and tetrachloropyridazine.

2,2',5,6,6'-Pentachloro-4,4'-dipyrimidinylamine (Compound No. 3, Table I) from 4-amino-2,5,6-trichloropyrimidine and 2,4,6-trichloropyrimidine.

2',4,6,6'-Tetrachloro-2,4'-dipyrimidinylamine (Compound No. 4, Table I) from 2-amino-4,6-dichloropyrimidine and 2,4,6-trichloropyrimidine.

2',4,5',6,6'-Pentachloro-2-4'-dipyrimidinylamine (Compound No. 5, Table I) from 2-amino-4,6-dichloropyrimidine and tetrachloropyrimidine.

4(4-Cyano-tetrafluoroanilino)-2,5,6-trichloropyrimidine (Compound No. 6, Table I) from pentafluorobenzonitrile and 4-amino-2,5,6-trichloropyrimidine.

2(4-Cyano-tetrafluoroanilino)-3,5,6-trifluoropyrazine (Compound No. 8, Table I) from 4-amino-tetrafluorobenzonitrile and tetrafluoropyrazine.

4-Pentafluoroanilino-2,5,6-trichloropyrimidine (Compound No. 9, Table I) from pentafluorobenzonitrile and 4-amino-2,5,6-trichloropyrimidine.

2,4',5,6,6'-Pentachloro-4,5'-dipyrimidinylamine (Compound No. 10, Table I) from 5-amino-4,6-dichloropyrimidine and tetrachlorpyrimidine.

4-Pentafluoroanilino-2,6-dichloropyrimidine (Compound No. 11, Table I) from pentafluoroaniline and 2,4,6-trichlorpyrimidine.

4(4-Nitro-tetrafluoroanilino)-2,5,6-trichloropyrimidine (Compound No. 12, Table I) from 4-amino-2,5,6-trichloropyrimidine and pentafluoronitrobenzene.

4(4-Nitro-2-trifluoromethylanilino)-2,5,6-trichloropyrimidine (Compound No. 13, Table I) from 2-Amino-4-nitrobenzotrifluoride and tetrachloropyrimidine.

5(4-Cyano-tetrafluoroanilino)-4,6-dichloropyrimidine (Compound No. 14, Table I) for pentafluorobenzonitrile and 5-amino-4,6-dichloropyrimidine.

4(2-Heptafluoronaphthylamino)-2,5,6-trichloropyrimidine, or the corresponding 1-heptafluoronaphthylamino isomer, (Compound No. 15, Table I) from octafluoronaphthalene and 4-amino-2,5,6-trichloropyrimidine.

4(4-Cyano-tetrafluoroanilino)-3,5,6-trichloropyridazine, or the corresponding 3-pyridazine isomer, (Compound No. 16, Table I) from tetrachloropyridazine and 4-amino-tetrafluorobenzonitrile.

5(4-Cyano-tetrafluoroanilino)-3,4-dichloropyridazine, or the corresponding 3- or 4-pyridazine isomer, (Compound No. 17, Table I) from 3,4,5-trichloropyridazine and 4-amino-tetrafluorobenzonitrile.

2(3,5-Dichloro-2,6-difluoropyrid-4-ylamino)-trifluoropyrazine (Compound No. 18 Table I) from tetrafluoropyrazine and 4-amino-3,5-dichloro-2,6-difluoropyridine.

5(4-Nitro-2-trifluoromethylanilino)-4,6-dichloropyrimidine (Compound No. 19 Table I) from 5-amino-4,6-dichlorpyrimidine and 2-chloro-5-nitrobenzotrifluoride.

5(4-Nitro-tetrafluoroanilino)-4,6-dichloropyrimidine (Compound No. 20, Table I) from pentafluoronitrobenzene and 5-amino-4,6-dichloropyrimidine.

5-Cyano-2-methyl-2',5',6'-trichloro-4,4'-dipyrimidinylamine (Compound No. 21, Table I) from 4-amino-2,5,6-trichloropyrimidine and 4-chloro-5-cyano-2-methylpyrimidine.

2(3,5-Dichloro-2,6-difluoropyrid-4-ylamino)-6-chloropyrazine (Compound No. 22, Table I) from 2,6-dichloropyrazine and 4-amino-3,5-dichloro-2,6-difluoropyridine.

5-Cyano-4(3,5-dichloro-2,6-difluoropyrid-4-ylamino)-2-methylpyrimidine (Compound No. 23, Table I) from 4-chloro-5-cyano-2-methyl-pyrimidine and 4-amino-3,5-dichloro-2,6-difluoropyridine.

2,6-Dichloro-4(4-trifluoromethyl-tetrafluoroanilino)pyrimidine (Compound No. 24, Table I) from 4-amino-2,6-dichloropyrimidine and octafluorotoluene.

4(4-Cyano-tetrafluoroanilino)-2,6-dichloropyrimidine (Compound No. 25, Table I) from pentafluorobenzonitrile and 4-amino-2,6-dichloropyrimidine.

4(3,5-Dichloro-2-fluoro-6-methylthio-pyrid-4-ylamino)-2,5,6-trichloropyrimidine (Compound No. 26, Table I) from tetrachloropyrimidine and 4-amino-3,5-dichloro-2-fluoro-6-methylthiopyridine.

2-Benzylthio-5-cyano-4(3,5-dichloro-2,6-difluoropyrid-4-ylamino)pyrimidine (Compound No. 27, Table I) from 4-amino-3,5-dichloro-2,6-difluoro-pyridine and 2-benzylthio-4-chloro-5-cyanopyrimidine.

4(3,5-Dichloro-2-fluoro-6-methoxypyrid-4-ylamino)-2,5,6-trichloropyrimidine (Compound No. 28, Table I) from 4-amino-3,5-dichloro-2-fluoro-6-methoxypyridine and tetrachloropyrimidine.

4(2-bromo-4-nitroanilino)-2,5,6-trichloropyrimidine (Compound No. 29, Table I) from 2-bromo-4-nitroaniline and tetrachloropyrimidine.

2(4-Nitro-2-trifluoromethylanilino)-trifluoropyrazine (Compound No. 30, Table I) from tetrafluoropyrazine and 2-amino-5-nitrobenzotrifluoride.

4(3,5-Dichloro-2,6-difluoropyrid-4-ylamino)-trifluoropyridazine (Compound No. 31, Table I) from tetrafluoropyridazine and 4-amino-3,5-dichloro-2,6-difluoropyridine.

4(4-Nitro-2-trifluoromethylanilino)-trifluoropyridazine (Compound No. 32, Table I) from 2-Amino-5-nitrobenzotrifluoride and tetrafluoropyridazine.

6-Chloro-3',5',6'-trifluoro-2,2'-dipyrazinylamine (Compound No. 33, Table I) from 2-Amino-6-chloropyrazine and tetrafluoropyrazine.

A mixture of 4(2-amino-3,5-dichloro-6-fluoropyrid-4-ylamino)-2,5,6-trichloropyrimidine and 4(4-amino-3,5-dichloro-6-fluoropyrid-2-ylamino)-2,5,6-trichloropyrimidine (Compound No. 34, Table I) from 2,4-diamino-3,5-dichloro-6-fluoropyridine and tetrachloropyrimidine.

5-Cyano-4(4-cyano-tetrafluoroanilino)-2-trifluoromethylpyrimidine (Compound No. 35, Table I) from 4-chloro-5-cyano-2-trifluoromethylpyrimidine and 4-amino-tetrafluorobenzonitrile.

5Cyano-4(3,5-dichloro-2,6-difluoropyrid-4-ylamino)-2-trifluoromethyl pyrimidine (Compound No. 36, Table I) from 4-chloro-5-cyano-2-trifluoromethylpyrimidine and 4-amino-3,5-dichloro-2,6-difluoropyridine.

2-Benzylthio-5-cyano-4(4-cyano-tetrafluoroanilino)pyrimidine (Compound No. 37, Table I) from 2-benzylthio-4-chloro-5-cyanopyrimidine and 4-amino-tetrafluorobenzonitrile.

6-Chloro-4(3,5-dichloro-2,6-difluoropyrid-4-ylamino)-2-trifluoromethylpyrimidine (Compound No. 38, Table I) from 4,6-dichloro-2-trifluoromethylpyrimidine and 4-amino-3,5-dichloro-2,6-difluoropyridine.

2(3,5-Dichloro-2-fluoro-6-methoxypyrid-4-ylamino)-trifluoro-pyrazine (Compound No. 39, Table I) from 4-amino-3,5-dichloro-2-fluoro-6-methoxypyridine and tetrafluoropyrazine.

4(3,5-Dichloro-2-fluoro-6-methoxypyrid-4-ylamino)-trifluoropyridazine (Compound No. 40, Table I) from 4-amino-3,5-dichloro-2-fluoro-6-methoxypyridine and tetrafluorobenzonitrile.

EXAMPLE 4

The activity of a number of the compounds was tested against a variety of insect and other invertebrate pests. The compounds were used in the form of liquid preparations containing 0.1% by weight of the compound except in the tests with *Aedes aegypti* and *Meloidogyne incognita* where the preparations contain 0.1% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "LISSAPOL" is a registered Trade Mark.

The test procedure adopted with regard to each pest was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table 2. In this table the first column indicates the name of the pest species.

Each of the subsequent columns indicates the host plant or medium on which it was supported, the number of days which were allowed to elapse after the treatment before assessing the mortality of the pests, and the results obtained for each of the compounds, numbered as in Table I above. The assessment is expressed in integers which range from 0–3.

0 represents less than 30% kill
1 represents 30–49% kill
2 represents 50–90% kill
3 represents over 90% kill A dash (—) in Table 2 indicates that no test was carried out. The symbol "A" in Table 2 indicates that an antifeeding effect was observed.

TABLE 2

| Pest Species | Support Medium | No. of days | 1 | 4 | 6 | 7 | 8 | 9 | 12 | 14 | 16 | 17 | 18 | 21 | 22 | 23 | 24 | 25 | 26 | 27 |
|---|---|---|---|---|---|---|---|---|---|---|---|---|---|---|---|---|---|---|---|---|
| | | | | | | | | | Compound No. (Table 1) | | | | | | | | | | | |
| *Tetranychus telarius* (red spider mites, adults) | French Bean | 3 | 3 | 0 | 3 | 3 | 3 | 2 | 3 | 3 | 3 | 3 | 3 | 0 | 0 | 3 | 3 | 3 | 1 | 3 |
| *Tetranychus telarius* (red spider mites, eggs) | French Bean | 3 | 0 | 0 | 0 | 0 | 0 | 0 | 3 | 0 | 0 | 0 | 0 | 0 | 0 | 3 | 3 | 3 | 2 | 3 |
| *Aphis fabae* (green aphids) | Broad Bean | 2 | 3 | 0 | — | 2 | 3 | 0 | 0 | 0 | 0 | 0 | 0 | 2 | 0 | 0 | 0 | 0 | 0 | 0 |
| *Megoura viceae* (black aphids) | Broad Bean | 2 | 3 | 0 | — | 0 | 3 | 0 | 0 | 0 | 0 | 0 | 0 | 3 | 0 | 0 | 0 | 0 | 0 | 0 |
| *Aedes aegypti* (mosquito larvae) | Water | 1 | 0 | 0 | 0 | 0 | 0 | 0 | 0 | 0 | 0 | 0 | 0 | 0 | 0 | 0 | 0 | 0 | 0 | 0 |
| *Musca domestica* (houseflies-contact test*) | Milk/sugar | 2 | 0 | 1 | 2 | 2 | 0 | 0 | 1 | 0 | 0 | 0 | 0 | 2 | 0 | 0 | 0 | 0 | 0 | 0 |
| *Musca domestica* (houseflies-residual test*) | Plywood | 2 | 0 | 0 | 0 | 0 | 0 | 0 | 0 | 0 | 0 | 0 | 0 | 0 | 0 | 0 | 0 | 0 | 1 | 0 |
| *Blattella germanica* (cockroaches) | — | 1 | — | — | — | — | — | — | — | — | — | — | — | — | 0 | — | 0 | 0 | 0 | 0 |
| *Pieris brassicae* (cabbage white caterpillers) | Cabbage | 2 | 0 A | 0 | 0 | 0 | 0 | 0 | 0 | 0 | 0 | 0 | 0 | 0 | 3 A | 2 A | 0 A | 2 A | 0 A | 0 A |
| *Plutella maculipennis* (diamond back moth, larvae) | Mustard | 2 | 0 | 0 A | 0 A | 0 A | 0 | 0 | 0 A | 0 A | 0 | 0 A | 0 | 0 | 0 | 0 | 0 A | 0 A | 0 | 0 |
| *Phaedon cochleariae* (mustard beetles) | Mustard | 2 | 0 | 0 | 0 | 0 | 0 | 0 | 0 | 0 | 0 | 0 | 0 | 0 | 0 | 0 | 0 | 0 A | 0 A | 0 |
| *Meloidogyne incognita* (nematodes) | Water | 1 | — | — | — | — | — | — | — | — | — | — | — | 2 | — | — | — | — | 3 | 3 |

| Pest Species | Support Medium | No. of days | 30 | 31 | 32 | 33 | 34 | 35 | 36 | 37 | 38 | 39 | 40 |
|---|---|---|---|---|---|---|---|---|---|---|---|---|---|
| | | | Compound No: (Table 1) | | | | | | | | | | |
| *Tetranychus telarius* (red spider mites, adults) | French Bean | 3 | 3 | 3 | 1 | 0 | 0 | 0 | 3 | 0 | 0 | 2 | 3 |
| *Tetranychus telarius* (red spider mites, eggs) | French Bean | 3 | 3 | 0 | 0 | 0 | 0 | 0 | 3 | 0 | 3 | 0 | 0 |
| *Aphis fabae* (green aphids) | Broad Bean | 2 | 0 | 0 | 0 | 0 | 0 | 0 | 3 | 0 | 3 | 0 | 0 |
| *Megoura viceae* (black aphids) | Broad Bean | 2 | 0 | 0 | 0 | 0 | 0 | 0 | 3 | 0 | 3 | 0 | 0 |
| *Aedes aegypti* (mosquito larvae) | Water | 1 | 1 | 0 | 0 | 0 | 0 | 0 | 0 | 0 | 3 | 0 | 0 |
| *Musca domestica* (houseflies-contact test*) | Milk/sugar | 2 | 0 | 0 | 0 | 0 | 0 | 0 | 2 | 0 | 2 | 0 | 0 |
| *Musca domestica* (houseflies-residual test*) | Plywood | 2 | 0 | 0 | 0 | 0 | 0 | 0 | 0 | 0 | 0 | 0 | 0 |
| *Blattella germanica* (cockroaches) | — | 1 | 0 | 0 | 0 | 0 | — | — | 2 | — | 2 | — | 0 |
| *Pieris brassicae* (cabbage white caterpillars) | Cabbage | 2 | 0 | 0 A | 0 A | 0 | 0 A | 2 A | 3 A | 0 A | 3 A | 0 A | 0 A |
| *Plutella maculipennis* (diamond back moth, larvae) | Mustard | 2 | 0 | 0 A | 0 A | 3 A | 0 | 0 | 1 A | 1 A | 0 | 0 | 0 |
| *Phaedon cochleariae* (mustard beetles) | Mustard | 2 | 0 | 0 | 0 | 0 | 0 | 0 | 0 | 0 | 0 A | 0 | 0 |
| *Meloidogyne incognita* (nematodes) | Water | 1 | — | — | 3 | — | — | — | — | — | — | — | — |

*In the contact test the flies are sprayed directly; in the residual test the flies are placed on a medium that had previously been treated.

EXAMPLE 5

Compounds of the invention were tested for molluscicidal activity and details of the tests conducted are as follows.

A weighed sample of the compound under test was dissolved in 0.5 cc. of an ethanol and acetone mixture (50:50 v/v). The solution was diluted with 0.5 cc. water and poured on to a calf feeding pellet in a glass petri dish and the pellet was air dried for 24 hours. The weight of compound used was chosen so that the dried pellet contained 4% by weight of the active ingredient. Two replicates each consisting of a plastic petri dish containing a pellet, 2 slugs, and a moistened filter paper to maintain a high relative humidity were used in each test. The dishes were left in the cold room (10°C). After 6 days the kill was assessed.

The slugs used were Agriolimax reticulatus (Mull), and they had been starved for 24 hours before the commencement of the tests. The results of the test are set out in Table 3 below.

TABLE 3

| Compound No. (Table I) | % kill of slugs |
|---|---|
| 1 | 100 |
| 2 | 50 |
| 13 | 50 |
| 18 | 100 |
| 26 | 50 |
| 36 | 50 |
| 38 | 50 |

EXAMPLE 6

The compounds of this invention were tested against a variety of foliar fungal diseases of plants. The technique employed is to spray the foliage of the undiseased plants with a solution of the test compound and also to drench the soil in which the plants are growing with another solution of the same test compound. All solution for spraying and drenching contained 0.01% of the test compound. The plants were then infected with the disease it was desired to control and after a period of days, depending upon the particular disease, the extent of the disease was visually assessed. The results are given in Table 4.a, below, wherein the extent of the disease is given in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |

In Table 4 the disease is given in the first column, and in the second column is given the time which elapsed between infecting the plants and assessing the amount of disease.

TABLE 4

| Disease and Plant | Time Interval (days) | Disease Code Letter (Table 4a) |
|---|---|---|
| Puccinia recondita (wheat) | 10 | A |
| Phytophthora infestans (tomato) | 3 | B |
| Plasmopara viticola (vine) | 7 | C |
| Podosphaera leucotricha (apple) | 10 | D |
| Uncinula necator (vine) | 10 | E |
| Botrytis cinorea (bean) | 3 | F |

Table 4a

| No. of Compound (Table I) | Disease Code Letter (Table 4) | | | | | |
|---|---|---|---|---|---|---|
| | A | B | C | D | E | F |
| 1 | 0 | — | 3 | — | — | — |
| 2 | 0 | 3 | 3 | 3 | 2 | — |
| 3 | 2 | 0 | 2 | 0 | 0 | 3 |
| 4 | 0 | 0 | 0 | 1 | 0 | 1 |
| 5 | 0 | 0 | 3 | 0 | 0 | 0 |
| 6 | 2 | — | 3 | 3 | — | — |
| 7 | 3 | — | 3 | 3 | — | — |
| 8 | 2 | — | 3 | 3 | — | 3 |
| 9 | 1 | — | 3 | 3 | — | 3 |
| 10 | 0 | — | 0 | — | 0 | 2 |
| 11 | 0 | — | 3 | — | 3 | 0 |
| 12 | 2 | — | 3 | 3 | — | — |
| 13 | 0 | — | 3 | — | 3 | 3 |
| 14 | 0 | 3 | 3 | — | 0 | 3 |
| 15 | 0 | 3 | 3 | — | 3 | 0 |
| 16 | 0 | 3 | 3 | — | 3 | 1 |
| 18 | 1 | 3 | 3 | — | 3 | 2 |
| 19 | 0 | 0 | 3 | — | 0 | 2 |
| 20 | 0 | 3 | 3 | — | 2 | 3 |
| 21 | 0 | 2 | 3 | 1 | 3 | 1 |
| 22 | 0 | 0 | 1 | 0 | 3 | 0 |
| 23 | 3 | — | 1 | — | — | — |
| 24 | 0 | — | 3 | 3 | 3 | 3 |
| 25 | 2 | — | 3 | 1 | 3 | 3 |
| 26 | 2 | 3 | 3 | 3 | 3 | 3 |
| 27 | 0 | 1 | 3 | 0 | 0 | 0 |
| 28 | 0 | 3 | 3 | 0 | 1 | 3 |
| 29 | 0 | 1 | 3 | 0 | 0 | 1 |
| 30 | 1 | — | — | 1 | 1 | 1 |
| 31 | 2 | — | — | — | — | 1 |
| 32 | 2 | — | — | 3 | 0 | 3 |
| 33 | 1 | 2 | 0 | 2 | 0 | 1 |
| 34 | 0 | 3 | 3 | 0 | 0 | 1 |
| 35 | 1 | 3 | 3 | 3 | 2 | 0 |
| 37 | 3 | 3 | 3 | 1 | 2 | 0 |
| 38 | — | — | 3 | — | — | 2 |
| 39 | — | 2 | 3 | — | — | 1 |
| 40 | — | 3 | 3 | — | — | 2 |

EXAMPLE 7

The culture Fusarium culmorum was maintained on 2% malt agar test tube slopes at 20°C. Thirteen to seventeen days prior to testing the chemical, the culture was transferred to soil cornmeals, which consisted of 400 grams of 5% maize meal in John Innes seed compost contained in a ½ pint bottle. The cornmeals were plugged with cotton wool and sterilized in an autoclave for 2 hours, before inoculation. Two days prior to testing the chemical, the seeds and the soil were prepared. The soil was prepared by mixing the cornmeals with John Innes seed compost at the rate of 2 cornmeals to 3 buckets of compost (2 gallon capacity buckets). The seeds were prepared by rolling 10 grams of wheat seeds in a 25% china clay formulation of the chemical (where the chemical was a powder) or a 12.5% china clay formulation (where the chemical was a liquid) at the rate of 1000 ppm weight/weight, e.g. 40 milligrams of 25% formulation on 10 grams of seeds. To test the chemical approximately 100 grams of the mixed soil was placed in a fibre pot, twenty seeds were placed on the surface and a further approximate 100 grams were placed on top of the seeds. This was repeated 3 times making four replicates in all. The pots were maintained in the greenhouse between 16°C and 20°C. After 10 days the number of germinated seeds was recorded and after 17 days the roots were uncovered and the number healthy recorded. These recordings were compared with untreated seeds and seeds treated with mercury (Agrosan) and calculations were made to obtain a grading for disease control. The gradings used were the same as those of the previous Example, and the results are given in Table 5 below.

TABLE 5

| Compound No: (Table I) | Grading | Compound No: (Table I) | Grading |
|---|---|---|---|
| 6 | 1 | 19 | 2 |
| 8 | 2 | 20 | 1 |
| 9 | 1 | 21 | 3 |
| 11 | 1 | 26 | 1 |

EXAMPLE 8

The culture Rhizoctonia solani was maintained on soil cornmeals, which consisted of 400 grams of 5% maize meal in John Innes seed compost contained in a ½ pint bottle. The cornmeals were plugged with cotton wool and sterilized in an autoclave for 2 hours before inoculation. Nine days prior to testing the chemical, the soil was prepared by mixing the cornmeals with John Innes seed compost at the rate of 1 cornmeal to 1½ buckets of compost (2 gallon capacity buckets). Four days before testing the chemical, it was mixed with 400 grams of soil in a quart bottle at the rate of 100 ppm weight/weight.

Approximately 100 grams of John Innes seed compost was placed in a fibre pot, eight cotton seeds were placed on the surface, and 100 grams of the mixed soil was placed on top of the seeds. This was repeated three times, making four replicates in all. After 13 days the seedlings were assessed for disease. These assessments were compared with untreated seeds and calculations were made to obtain a grading for disease control. The gradings used were the same as those of the previous two examples, and the results are set out in Table 6.

TABLE 6

| Compound No. (Table I) | Grading | Compound No. (Table I) | Grading |
| --- | --- | --- | --- |
| 4 | 1 | 20 | 3 |
| 6 | 3 | 25 | 1 |
| 8 | 2 | 26 | 1 |
| 11 | 1 | 30 | 1 |
| 13 | 3 | 32 | 1 |
| 15 | 3 | | |

EXAMPLE 9

This example illustrates the use of invention compounds in combatting the disease Verticillium albo-atrum in a systemic manner.

The chemical to be tested is incorporated into sterile John Innes seed compost at the rate of 100 ppm per weight of soil. The soil and chemical are mixed thoroughly in glass powder jars by ball-milling the jars for 20 minutes. The jars are then left to stand for two days.

Four replicate, 1.5 inches diameter, disposable, plastic pots are half filled with sterile John Innes Seed Compost and into each pot are placed between six and ten cotton seeds. The cotton seeds are then covered with the soil with the chemical incorporated. The seeds are then incubated at 30°C for three to four weeks.

A spore suspension of Verticillium albo-atrum is prepared and washed twice using sterile water. The pore suspension concentration is then adjusted to give $10^6$ spore per milliliter.

The cotton plants in the pots are thinned out to give four plants per pot. One pot of the four replicate pots is placed on one side to act as a phytotoxic test for the chemical.

The plants in the remaining three replicate pots are injected with 0.1 milliliter of spore suspension into the stem vascular tissue one inch above the soil level using a sterile syringe.

Assessments are made on the plants one week later. Visual wilt symptoms and examination for brown staining on the vascular tissue are carried out and the number of healthy plants are recorded.

The chemical treatments are graded on a 0-3 scale and a grade of 3 indicates good control of Verticillium albo-atrum while a grade of 0 indicates no appreciable control of the disease when compared to an untreated control. The results are given in Table 7 below.

TABLE 7

| Compound No: (Table I) | Grading |
| --- | --- |
| 1 | 2 |
| 13 | 1 |
| 26 | 3 |

EXAMPLE 10

The activity of the compound of the invention against a wide variety of plant bacterial diseases and fungal post-harvest saprophytic diseases was investigated by in vitro tests as follows. 5 mg. of the compound under test was dissolved or suspended in 10 cc. of acetone and 2 cc. of this solution or suspension was added to 18 cc. of nutrient agar (for the bacterial diseases) or 16 cc. of 2% malt agar (for the fungal diseases) to give a final concentration of 50 parts per million of the compound under test. 2 cc. of a streptomycin preparation containing 100 units/cc. was added to the malt agar to prevent bacterial contamination of the fungal tests.

The agar preparations were dried overnight in petri dishes and inoculated the following morning with the bacterial or fungal diseases using a multipoint inoculator. The antibacterial activity was assessed after 5 days and the antifungal activity after 6 days.

The results of the tests are set out below in Table 9 (antibacterial activity) and Table 10 (antifungal activity). The results are graded as in Example 6 above. The names of the disease organisms are indicated in Table 8.

TABLE 8

| Bacterial Disease Organism | Code Table 9 | Fungal Disease Organism | Code Table 10 |
| --- | --- | --- | --- |
| Agrobacterium tumifaciens | B1 | Nigrospora sphaerica | F1 |
| Corynebacterium michiganense | B2 | Phytophthora Citrophthora | F2 |
| Xanthomonas malvacearum | B3 | Alternaria citri | F3 |
| Erwinia carotovora | B4 | Diplodia natalensis | F4 |
| Xanthomonas oryzae | B5 | Phomopasis citri | F5 |
| Pseudomonas syringae | B6 | Ceratosystis paradoxa | F6 |
| Streptomyces scabies | B7 | Gloeosporium musarum | F7 |
| Pseudomonas mors prunerum | B8 | Penicillium digitatum | F8 |
| Pseudomonas phaseolicola | B9 | Phoma exigua | F9 |
| Erwinia amylovora | B10 | Botrytis tulipae | F10 |
| | | Botrodiplodia theobromae | F11 |
| | | Fusarium caeruleum | F12 |

TABLE 9

| Compound No. (Table I) | B1 | B2 | B3 | B4 | B5 | B6 | B7 | B8 | B9 | B10 |
| --- | --- | --- | --- | --- | --- | --- | --- | --- | --- | --- |
| 2 | 2 | 3 | 0 | 0 | 2 | 2 | 2 | 0 | 0 | 0 |
| 3 | 0 | 2 | 0 | 0 | 0 | 1 | 2 | 0 | 0 | 0 |
| 4 | 0 | 0 | 2 | 0 | 2 | 0 | 2 | 0 | 0 | 0 |
| 5 | 0 | 0 | 0 | 0 | 0 | 2 | 2 | 0 | 0 | 0 |
| 8 | 3 | 3 | 3 | 0 | 3 | 2 | 2 | 2 | 2 | 2 |
| 10 | 0 | 2 | 0 | 0 | 0 | 2 | 2 | 0 | 0 | 0 |
| 15 | 0 | 2 | 1 | 0 | 0 | 3 | 2 | 0 | 0 | 2 |
| 24 | 0 | 2 | 3 | 0 | 0 | 2 | 2 | 0 | 0 | 0 |
| 26 | 0 | 1 | 0 | 0 | 0 | 1 | 2 | 1 | 2 | 2 |
| 28 | 0 | 2 | 0 | 0 | 0 | 0 | 0 | 0 | 0 | 0 |

TABLE 10

| Compound No. (Table 1) | F1 | F2 | F3 | F4 | F5 | F6 | F7 | F8 | F9 | F10 | F11 | F12 |
| --- | --- | --- | --- | --- | --- | --- | --- | --- | --- | --- | --- | --- |
| 2 | 3 | 3 | 3 | 3 | 3 | 3 | 3 | 3 | 3 | — | — | 3 |
| 3 | 3 | 3 | 3 | 0 | 0 | 0 | 2 | 0 | 0 | — | — | 3 |
| 4 | 3 | 3 | 2 | 0 | 0 | 0 | 0 | 0 | 0 | — | — | 0 |
| 8 | 3 | 3 | 3 | 3 | 3 | 3 | 3 | 3 | 3 | 3 | 3 | 3 |
| 10 | 3 | 3 | 3 | 0 | 0 | 0 | 2 | 0 | 0 | — | — | 3 |

TABLE 10-continued

| Compound No. (Table 1) | F1 | F2 | F3 | F4 | F5 | F6 | F7 | F8 | F9 | F10 | F11 | F12 |
|---|---|---|---|---|---|---|---|---|---|---|---|---|
| 24 | 3 | 2 | 3 | 3 | 3 | 0 | 3 | 3 | 3 | 3 | 0 | 3 |
| 26 | 3 | 2 | 0 | 0 | 2 | 0 | 0 | 0 | 0 | 0 | 3 | 0 |
| 28 | 3 | 0 | 2 | 0 | — | 0 | 0 | 0 | 0 | 0 | 2 | 0 |
| 29 | 3 | 3 | 2 | 0 | 3 | 1 | 1 | 0 | 0 | 0 | 0 | 0 |

EXAMPLE 11

This Example illustrates the herbicidal properties of the compounds of the present invention. The compounds were ball-milled in water containing a surface-active agent sold under the name of Lissapol and comprising a condensate of p-nonylphenol with seven to eight molar proportions of ethylene oxide. The ball-milled material was diluted with water to give a spray composition containing 0.1% of the surface-active agent, and sprayed on to young pot plants of the species listed in Table 11 below (Post-emergence test). The rate of application of the active ingredient was equivalent to 10 kilograms per hectare and the spray volume 100 gallons per acre. Damage to the plants was assessed on a scale of 0 to 3 where 0 represents no effect and 3 represents complete kill. In the same experiment pots of soil were sown with seeds of the same plant species and then sprayed with the above spray composition at the rate of 10 kilograms per hectare of active ingredient (pre-emergence test). The results are given in Table 11 below.

TABLE 11

| No. of Compound (Table 1) | Pre-emergence | | | | Post-emergence | | | |
|---|---|---|---|---|---|---|---|---|
| | Lettuce | Tomato | Wheat | Maize | Lettuce | Tomato | Wheat | Maize |
| 1 | 3 | 3 | 0 | 0 | 3 | 3 | 0 | 0 |
| 2 | 3 | 1 | 0 | 0 | 3 | 2 | 1 | 1 |
| 6 | 2 | 1 | 0 | 0 | 3 | 3 | 0 | 0 |
| 8 | 3 | 2 | 1 | 0 | 3 | 0 | 0 | 0 |
| 9 | 0 | 0 | 0 | 0 | 1 | 1 | 0 | 0 |
| 16 | 3 | 0 | 0 | 0 | 0 | 0 | 0 | 0 |
| 17 | 3 | 1 | 0 | 0 | 3 | 0 | 0 | 0 |
| 18 | 3 | 0 | 0 | 0 | 1 | 1 | 0 | 0 |
| 22 | 0 | 0 | 0 | 0 | 0 | 2 | 0 | 0 |
| 23 | 3 | 1 | 0 | 0 | 0 | 1 | 0 | 0 |
| 24 | 1 | 0 | 0 | 0 | 1 | 0 | 0 | 0 |
| 25 | 3 | 2 | 0 | 0 | 3 | 0 | 0 | 1 |
| 30 | 3 | 0 | 0 | 0 | 1 | 0 | 0 | 0 |
| 31 | 3 | 3 | 0 | 1 | 1 | 1 | 0 | 1 |
| 32 | 2 | 0 | 0 | 0 | 1 | 0 | 0 | 0 |
| 36 | 3 | 3 | 3 | 3 | 3 | 3 | 0 | 0 |
| 38 | 3 | 1 | 0 | 0 | 3 | 3 | 0 | 1 |

These results demonstrate that the compounds of this invention have herbicidal properties, and also that some compounds have particularly useful selective herbicidal activity against broad-leaved plants.

Compounds Nos. 1 and 36 were sprayed onto a further group of plant species in a test conducted in the same way as the preceding test; the results, which are given in Table 12 below are graded on a scale of 0 to 5, where 0 indicates no effect and 5 indicates complete kill of the plants.

TABLE 12

| Compound No. (Table 1) | Pre-Emergence | | | | | | | |
|---|---|---|---|---|---|---|---|---|
| | Sb | Ka | Ca | Pea | On | Bar | Ri | Oat |
| 1 | 1 | 1 | 4 | 0 | 2 | 0 | 1 | 0 |
| 36 | 0 | 0 | 0 | 0 | 0 | 0 | 0 | 0 |
| | Post-Emergence | | | | | | | |
| 1 | 1 | 1 | 2 | 0 | — | 0 | 0 | 0 |
| 36 | 3 | 3 | 5 | 2 | — | 2 | 1 | 1 |

The abbreviations used in Table 12 have the following meanings.

| Abbreviation | Plant |
|---|---|
| Sb | Sugar Beet |
| Ka | Kale |
| Ca | Cabbage |
| On | Onion |
| Bar | Barley |
| Ri | Rice |

EXAMPLE 12

This Example illustrates a concentrate comprising a miscible oil which is readily convertible by dilution with water into a liquid preparation suitable for spraying purposes.

The concentrate has the following composition:

| | % wt. |
|---|---|
| Compound No.1 of Table I | 25.0 |
| 'LUBROL' L (alkylphenol/ethylene oxide condensate; 'Lubrol' is a Trade Mark) | 2.5 |
| Calcium dodecylbenzenesulphonate | 2.5 |
| 'AROMASOL' H (alkylbenzenesolvent; 'Aromasol' is a Trade Mark) | 70.0 |
| | 100.0 |

EXAMPLE 13

This example also illustrates a concentrate which is in the form of a miscible oil. The composition of this concentrate is as follows:

| | % wt. |
|---|---|
| Compound No.2 of Table I | 25.0 |

-continued

| | |
|---|---|
| 'LUBROL' L ('Lubrol' is a Trade Mark) | 4.0 |
| Calcium dodecylbenzenesulphonate | 6.0 |
| 'AROMASOL' H ('Aromasol' is a Trade Mark) | 65.0 |
| | 100.0 |

EXAMPLE 14

This Example illustrates a wettable powder having the following composition:

| | % wt. |
|---|---|
| Compound No.3 of Table I | 25.0 |
| Sodium silicate | 5.0 |
| Calcium lignosulphonate | 5.0 |
| China clay | 65.0 |
| | 100.0 |

EXAMPLE 15

This Example illustrates an atomisable fluid comprising a mixture consisting of 25% by weight of the compound No. 4 of Table I and 75% by weight of xylene.

EXAMPLE 16

This Example illustrates a dusting powder which may be applied directly to plants or other surfaces and comprises 1% by weight of Compound No. 5 of Table I and 99% by weight of talc.

EXAMPLE 17

25 Parts by weight of Compound No. 6 of Table I, 65 parts by weight of xylene, and 10 parts of an alkyl aryl polyether alcohol 'Triton' X-100 ('Triton' is a Trade Mark) were mixed. There was thus obtained an emulsion concentrate which can be mixed with water to produce an emulsion suitable for use in agricultural applications.

EXAMPLE 18

5 Parts by weight of Compound No. 7 of Table I were thoroughly mixed in a suitable mixer with 95 parts by weight of talc. There was thus obtained a dusting powder.

EXAMPLE 19

10 Parts by weight of Compound No. 8 of Table I, 10 parts of an ethylene oxide-octylphenol condensate ('Lissapol' NX 'Lissapol' is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 20

This Example illustrates a concentrated liquid formulation in the form of an emulsion. The ingredients listed below were mixed together in the stated proportions and the whole stirred until the constituents were dissolved.

| | % wt. |
|---|---|
| Compound No.9 of Table I | 20 |
| 'LUBROL' L ('Lubrol' is a Trade Mark) | 17 |
| Calcium dodecylbenzenesulphonate | 3 |
| Ethylene dichloride | 45 |
| 'AROMASOL' H ('Aromasol' is a Trade Mark) | 15 |
| | 100 |

EXAMPLE 21

The ingredients listed below were ground together in the proportions stated to produce a powdered mixture readily dispersible in liquids.

| | % wt. |
|---|---|
| Compound No.10 of Table I | 50 |
| 'DISPERSOL' T ('Dispersol' is a Trade Mark) | 5 |
| China Clay | 45 |
| | 100 |

EXAMPLE 22

A composition in the form of grains readily dispersible in a liquid (for example water) was prepared by grinding together the first four of the ingredients listed below in the presence of water and then the sodium acetate was mixed in. The admixture was dried and passed through a British Standard mesh sieve, size 44–100 to obtain the desired size of grains.

| | % wt. |
|---|---|
| Compound No. 11 of Table I | 50 |
| 'DISPERSOL' T ('Dispersol' is a Trade Mark) | 12.5 |
| Calcium lignosulphonate | 5 |
| Calcium dodecylbenzenesulphonate | 12.5 |
| Sodium acetate | 20 |
| | 100 |

EXAMPLE 23

A composition suitable for use as a seed dressing was prepared by mixing all three of the ingredients set out below in the proportions stated.

| | % wt. |
|---|---|
| Compound No.12 of Table I | 80 |
| Mineral Oil | 2 |
| China Clay | 18 |
| | 100 |

EXAMPLE 24

A composition suitable for use as a seed dressing was prepared by mixing all three of the ingredients set out below in the proportions stated.

| | % wt. |
|---|---|
| Compound No.13 of Table I | 80 |
| Mineral Oil | 2 |
| China Clay | 18 |
| | 100 |

EXAMPLE 25

A granular composition was prepared by dissolving the active ingredient in a solvent, spraying the solution obtained onto granules of pumice and allowing the solvent to evaporate.

|  | % wt. |
|---|---|
| Compound No. 14 of Table I | 5 |
| Pumice Granules | 95 |
|  | 100 |

EXAMPLE 26

An aqueous dispersion formulation was prepared by mixing and grinding the ingredients recited below in the proportions stated.

|  | % wt. |
|---|---|
| Compound No. 15 of Table I | 40 |
| Calcium lignosulphonate | 10 |
| Water | 50 |
|  | 100 |

The following constitutes an explanation of the compositions or substances represented by the various Trade Marks and Trade Names referred to in the foregoing Examples.

| | |
|---|---|
| 'LUBROL' L | is a condensate of 1 mole of nonyl phenol with 13 molar proportions of ethylene oxide. |
| 'AROMASOL' H | is a solvent mixture of alkylbenzenes. |
| 'DISPERSOL' T | is a mixture of sodium sulphate and a condensate of formaldehyde with the sodium salt of naphthalene sulphonic acid. |
| 'LISSAPOL' NX | is a condensate of 1 mole of nonyl phenol with 8 moles of ethylene oxide. |

We claim:

1. A method of combatting insect, fungal and bacterial plant pests which comprises applying to said plants a pesticidally effective amount of a compound of the formula X—NH—Y wherein X is selected from the group consisting of a pyrazinyl radical bearing one to three substituents and a pyridazinyl radical bearing two to three substituents; and Y represents phenyl, naphthyl, pyridyl or diazinyl bearing at least one substituent; the substituents in each case being selected from the group consisting of halogen, cyano, nitro, trifluoromethyl, lower alkoxy, lower alkylthio, benzylthio, lower alkyl and amino; said compound bearing at least four substituents of which at least two are halogen atoms.

2. The method of claim 1 wherein the compound is of the formula X—NH—Y wherein X represents a halogen substituted diazinyl radical selected from the groups consisting of a pyrazinyl radical bearing from one to three halogens and a pyridazinyl radical bearing from two to three halogens; and Y is a substituted phenyl, naphthyl, pyridyl or diazinyl radical bearing at least two substituents selected from the group consisting of halogen, cyano, nitro, trifluoromethyl, methyl, methoxy, methylthio and amino.

3. A composition for combatting insect, fungal and bacterial plant pests comprising as active ingredient, a pesticidally effective amount of a compound of the formula X—NH—Y wherein X is selected from the group consisting of a pyrazinyl radical bearing one to three substituents and a pyridazinyl radical bearing two to three substituents; and Y represents phenyl, naphthyl, pyridyl or diazinyl bearing at least one substituent; the substituents in each case being selected from the group consisting of halogen, cyano, nitro, trifluoromethyl, lower alkoxy, lower alkylthio, benzylthio, lower alkyl and amino; said compound bearing at least four substituents of which at least two are halogen atoms and a major amount of a carrier for said compound.

4. A composition for combatting insect, fungal and bacterial plant pests comprising as active ingredient, a pesticidally effective amount of a compound of the formula X—NH—Y wherein X represents a halogen substituted diazinyl radical selected from the groups consisting of a pyrazinyl radical bearing from one to three halogens and a pyridazinyl radical bearing from two to three halogens; and Y is a substituted phenyl, naphthyl, pyridyl or diazinyl radical bearing at least two substituents selected from the group consisting of halogen, cyano, nitro, trifluoromethyl, methyl, methoxy, methylthio and amino.

* * * * *